US010813892B2

(12) United States Patent
McGinley et al.

(10) Patent No.: US 10,813,892 B2
(45) Date of Patent: Oct. 27, 2020

(54) ANTISEPTIC SOLUTIONS AND APPLICATORS

(71) Applicant: CAREFUSION 2200, INC., San Diego, CA (US)

(72) Inventors: Christopher McGinley, Highland Park, IL (US); Brandon Borowski, Winthrop Harbor, IL (US); Brandon Dellaringa, Arlington Heights, IL (US)

(73) Assignee: CAREFUSION 2200, INC., San Diego, CA (US)

( * ) Notice: Subject to any disclaimer, the term of this patent is extended or adjusted under 35 U.S.C. 154(b) by 0 days.

(21) Appl. No.: 15/163,500

(22) Filed: May 24, 2016

(65) Prior Publication Data
US 2017/0340585 A1  Nov. 30, 2017

(51) Int. Cl.
| | | |
|---|---|---|
| *A61K 31/155* | (2006.01) | |
| *A61K 47/12* | (2006.01) | |
| *A61K 47/02* | (2006.01) | |
| *A61K 9/00* | (2006.01) | |
| *A61K 9/08* | (2006.01) | |

(52) U.S. Cl.
CPC .......... *A61K 31/155* (2013.01); *A61K 9/0014* (2013.01); *A61K 9/08* (2013.01); *A61K 47/02* (2013.01); *A61K 47/12* (2013.01)

(58) Field of Classification Search
CPC ...... A61K 31/155; A61K 9/0014; A61K 9/08; A61K 47/02; A61K 47/12; A61K 8/36; A61K 2800/805; A61K 8/69; A61K 8/43; A61K 8/365; A61K 8/19; A61K 8/20; A61Q 17/005; A61M 35/003
See application file for complete search history.

(56) References Cited

U.S. PATENT DOCUMENTS

| | | | | |
|---|---|---|---|---|
| 4,219,333 | A | | 8/1980 | Harris |
| 5,171,523 | A | * | 12/1992 | Williams ................ A61L 2/18 206/205 |
| 5,605,934 | A | * | 2/1997 | Giertych .............. A61M 1/287 424/686 |
| 5,800,827 | A | | 9/1998 | Igarashi et al. |
| 2003/0195131 | A1 | | 10/2003 | Melrose et al. |
| 2008/0078046 | A1 | | 4/2008 | Reed |
| 2013/0316022 | A1 | | 11/2013 | Welsh et al. |
| 2014/0117274 | A1 | * | 5/2014 | Thomas .............. D06M 13/432 252/182.29 |

FOREIGN PATENT DOCUMENTS

WO   9831332 A1   7/1998

OTHER PUBLICATIONS

Adams et al., "Evaluation of 2% chlorhexidine gluconate in 70% isopropyl alcohol skin disinfectant," Journal of Hospital Infection (2005) 61, 287-290. (Year: 2005).*
Mohammadi, "Chlorhexidine gluconate, its properties and applications in endodontics," Iranian Endodontic Journal, 2008, pp. 113-125, vol. 2, No. 4.
Graham W. Denton: "Chlorhexidine" In: "Disinfection, sterilization, and preservation", Jan. 1, 2001 (Jan. 1, 2001), Lippincott [u.a.], Philadelphia, Pa. [u.a.], XP055519208, ISBN: 978-0-683-30740-5.).

* cited by examiner

*Primary Examiner* — Sarah Pihonak
*Assistant Examiner* — Jason Deck
(74) *Attorney, Agent, or Firm* — Arent Fox LLP

(57) ABSTRACT

An antiseptic solution comprising a pH-dependent antimicrobial agent, the pH-dependent antimicrobial agent having an operative pH range, wherein the solution has a pH on storage that is lower than the operative pH range. Applicators for applying the antiseptic solution and methods of using the antiseptic solution and applicators are also provided.

10 Claims, 10 Drawing Sheets

ANTISEPTIC SOLUTIONS AND APPLICATORS

BACKGROUND

Field

The present disclosure relates to antiseptic solutions and applicators, and methods of use thereof. More particularly, the present disclosure relates to an antiseptic solution comprising a pH-dependent antimicrobial agent having an operative pH range, wherein the solution has a pH on storage that is lower than the operative pH range, and applicators for applying the antiseptic solution to a surface.

Description of Related Art

Antiseptic solutions containing antimicrobial agents that may be applied, for example, to a patient's skin to kill bacteria prior to performing a medical procedure are known in the art. However, in existing antiseptic solutions, antimicrobial agents often degrade during manufacturing (e.g., sterilization) and/or over time, particularly in solutions that contain water. In many cases, the degradation rate of the antimicrobial agent is impacted by the pH of the antiseptic solution. In addition, the microbiological activity of the antimicrobial agent can also be impacted by the pH of the solution. Often, there is not a single pH value or pH range which allows both acceptable chemical stability and microbiological activity of the antimicrobial agent.

As such, when using applicators to apply antiseptic solutions known in the prior art, it may be difficult to provide both acceptable chemical stability on storage and microbiological activity upon application. For example, the pH necessary for acceptable chemical stability of an antiseptic solution may be different than the pH necessary for acceptable microbiological activity. Thus, there is a need in the art for an antiseptic solution and applicator that allows both acceptable chemical stability on storage and microbiological activity upon use of an antiseptic solution.

SUMMARY

In accordance with aspects of the present invention, an antiseptic may include a solution comprising a pH-dependent antimicrobial agent, the pH-dependent antimicrobial agent having an operative pH range, wherein the solution has a pH on storage that is lower than the operative pH range. According to some aspects, the solution may comprise a pH-lowering agent. According to some aspects, the solution may comprise a second pH upon activation, wherein the first pH is lower than the operative pH range, and the second pH is within the operative pH range.

In accordance to other aspects, an antiseptic solution may be provided in an applicator which may include a body, an internal chamber for containing the antiseptic solution, and an application member. According to some aspects, the applicator may further comprise an ampoule received in the internal chamber, wherein the antiseptic solution is contained within the ampoule. According to some aspects, the applicator may also comprise a pledget positioned between the application member and internal chamber, wherein the pledget may help control the rate liquid flows from the body, provide dye to the liquid, and/or prevent shards of glass from pushing through application member during use of the applicator. According to some aspects, the pledget and/or application member may be provided with an interaction agent so that when antiseptic solution passes through the pledget and/or application member, one or more components of the antiseptic solution interact with the interaction agent.

It will become readily apparent to those skilled in the art from the following detailed description, wherein it is shown and described only exemplary configurations of the antiseptic solution and applicator. As will be realized, the invention includes other and different aspects of an antiseptic solution and applicator and the various details presented throughout this disclosure are capable of modification in various other respects, all without departing from the spirit and scope of the invention. Accordingly, the drawings and the detailed description are to be regarded as illustrative in nature and not as restrictive.

DETAILED DESCRIPTION

Figure 1:
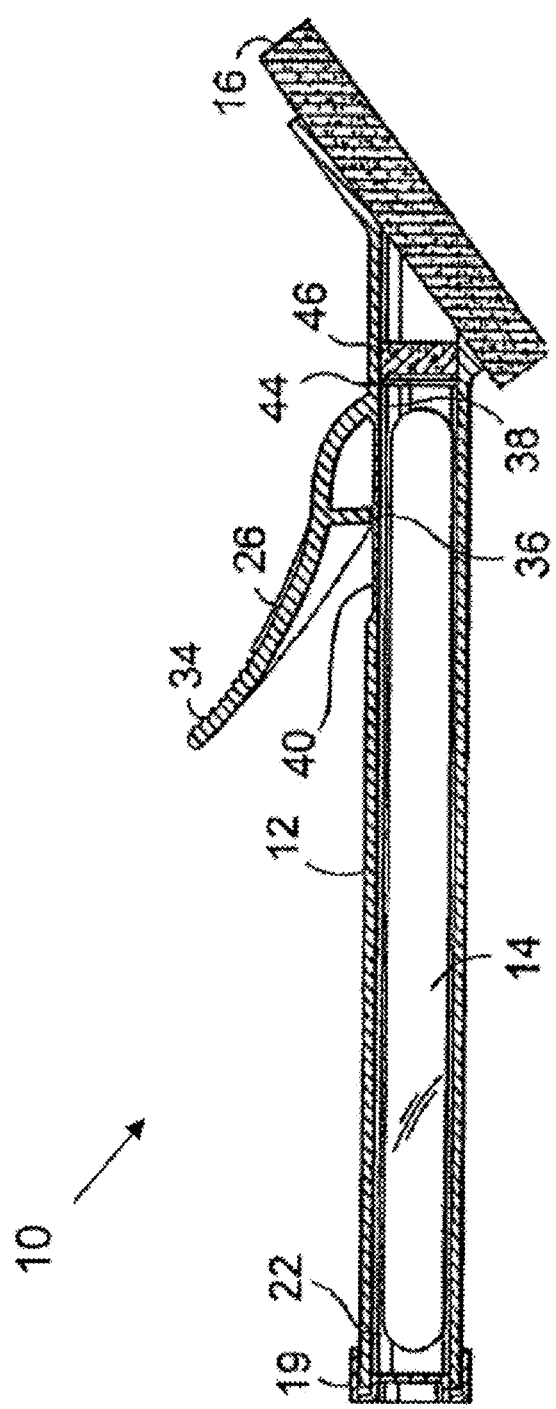
FIG. 1 is a side cutaway view of an antiseptic applicator having a pledget in accordance with certain aspects of the present invention.

In accordance with aspects of the present invention, an antiseptic may include a solution comprising a pH-dependent antimicrobial agent having an operative pH range.

As used herein, the term "about" means within ±10%, preferably ±5%, more preferably ±1% of the given value. As used herein, the term "stable" with respect to a solution means that there is no discernible precipitation, particulates, haziness, or cloudiness present in the solution, when viewed by the unaided human eye (i.e., that all of the components in the solution remain solubilized). As used herein, the term "unstable" with respect to a solution means that there is a discernible precipitation, particulates, haziness, and cloudiness present in the solution, when viewed by the unaided human eye (i.e., at least one of the components of the solution has become at least partially insolubilized). In other words, a "stable" solution appears clear to the naked eye while an unstable solution has at least some visible precipitation, particulate, haziness, or cloudiness.

As used herein, the term "pH-dependent antimicrobial agent" refers to an antimicrobial agent whose antimicrobial activity is affected by pH. According to some aspects, suitable pH-dependent antimicrobial agents include biguanides (e.g., chlorhexidine salts). According to some preferred aspects, the pH-dependent antimicrobial agent may comprise chlorhexidine and/or one or more salts thereof. For example, according to some aspects, the pH-dependent antimicrobial agent may be selected from the group consisting of chlorhexidine gluconate, chlorhexidine acetate, chlorhexidine, chlorhexidine hydrochloride, and any combination thereof.

Examples of biguanides/biguanide derivatives other than chlorhexidine/chlorhexidine salts include but are not limited to alexidine, alexidine salts, polyhexamide, polyhexamide salts, polyaminopropyl biguanide, polyaminopropyl biguanide salts, and other alkyl biguanides. As used herein, the term "derivative" refers to a) a chemical substance that is related structurally to a first chemical substance and derivable from it; b) a compound that is formed from a similar first compound or a compound that can be imagined to arise from another first compound, if one atom of the first compound is replaced with another atom or group of atoms; c) a compound derived or obtained from a parent compound and containing essential elements of the parent compound; or d) a chemical compound that may be produced from first compound of similar structure in one or more steps.

According to some aspects, the concentration of the pH-dependent antimicrobial agent in the antiseptic solution may vary depending on the specific pH-dependent antimicrobial species used or the desired antimicrobial effect. For example, according to some aspects, the concentration of the pH-dependent antimicrobial agent in the solution may be from about 0.01% to about 20% w/v, preferably from about 0.01% to about 10% w/v, even more preferably from about 0.01% to about 5%, even more preferably from about 0.5% to about 4%, and most preferably from about 1% to about 3% w/v. According to some aspects, the pH-dependent antimicrobial agent concentration in the solution may be from about 0.5% to about 2% w/v. According to some aspects, the pH-dependent antimicrobial agent concentration in the solution may be about 2% w/v.

According to some aspects, the pH-dependent antimicrobial agent may be provided in a solution comprising a solvent. According to some aspects, the solvent comprises an organic component. In some embodiments, the pH-dependent antimicrobial agent may be provided in a solution comprising at least one solvent comprising water and/or an alcohol, preferably isopropyl alcohol, ethyl alcohol, n-propyl alcohol, and any combination thereof.

According to some aspects, the concentration of the solvent in the solution may be from about 50% to about 99.99% v/v, preferably about 55% to about 90% v/v, more preferably about 60% to about 85% v/v, even more preferably about 65% to 75% v/v. According to some aspects, the solvent concentration in the solution may be about 70% v/v.

According to some aspects, the antiseptic solution may comprise 2% w/v chlorhexidine gluconate in 70% v/v isopropyl alcohol.

According to some aspects, the antiseptic solution may be aqueous. That is, the solvent of the solution is primarily water. As used herein, the term "aqueous" means at least about 50% v/v water, more preferably at least about 60% v/v water, more preferably at least about 70% v/v water, more preferably at least about 80% v/v water, more preferably at least about 90% v/v water, more preferably at least about 95% v/v, up to 100% v/v water. According to some aspects, when the solution is less than 100% v/v water, the remaining volume may include one or more additional solvents, for example, alcoholic solvents.

According to some aspects, the pH-dependent antimicrobial agent has an operative pH range. As used herein, the term "operative pH range" refers to the pH range of an antiseptic solution containing the pH-dependent antimicrobial agent where the pH-dependent antimicrobial agent exhibits acceptable microbiological activity. According to some aspects, the operative pH range may be the pH range of an antiseptic solution containing the pH-dependent antimicrobial agent where the pH-dependent antimicrobial agent kills at least 70% of the targeted microorganisms on a surface to which the antiseptic solution has been applied, preferably at least 75%, more preferably at least 80%, even more preferably at least 85%, even more preferably at least 90%, even more preferably at least 95%, and most preferably 100%.

According to some aspects, the operative pH range may be the pH range of an antiseptic solution containing the pH-dependent antimicrobial agent where the pH-dependent antimicrobial shows at least a 2 log reduction of targeted microorganisms on a surface to which the antiseptic solution has been applied, preferably at least a 3 log reduction, more preferably at least a 3.5 log reduction, and most preferably at least a 4 log reduction.

According to some aspects, the operative pH range may be a pH of at least 5.0, preferably at least 5.1, more preferably at least 5.2, even more preferably at least 5.3, even more preferably at least 5.4, and most preferably at least 5.5.

According to some aspects, the antiseptic solution has a pH on storage that is lower than the operative pH range. As used herein, the term "storage" refers to the storing of the antiseptic solution up to its point of use, or up to the point of activation, as described herein. According to some aspects, storage may refer to the period of time when the antiseptic solution is contained within a container. For example, according to some aspects, storage may refer to the period of time when the antiseptic solution is contained within the ampoule of an applicator. According to some aspects, the ampoule may be hermetically sealed. According to some aspects, the ampoule may comprise a material that minimizes the loss of gaseous components and/or prevents the antiseptic solution therein from contacting a surrounding environment.

According to some aspects, storage may require certain environmental conditions. For example, according to some aspects, storage may require certain temperature and/or relative humidity (RH) conditions. According to some aspects, storage may refer to environmental conditions of 25° C.±2° C. and 60% RH±5% RH. According to some aspects, storage may refer to environmental conditions of 30° C.±2° C. and 65% RH±5% RH. In some embodiments, storage may also or alternatively refer to conditions necessary for manufacture (e.g., elevated temperatures necessary for sterilization).

According to some aspects, the antiseptic solution has a pH on storage that is at least 0.1 pH units lower than the operative pH range, preferably at least 0.2 pH units lower than the operative pH range, more preferably at least 0.3 pH units lower than the operative pH range, even more preferably at least 0.4 pH units lower than the operative pH range, even more preferably at least 0.5 pH units lower than the operative pH range, even more preferably at least 0.6 pH units lower than the operative pH range, even more preferably at least 0.7 pH units lower than the operative pH range, even more preferably at least 0.8 pH units lower than the operative pH range, even more preferably at least 0.9 pH units lower than the operative pH range, and most preferably at least 1 pH unit lower than the operative pH range. According to some aspects, the antiseptic solution may have a pH on storage that is no more than 5.0.

According to some aspects, the antiseptic solution may have a pH on storage such that the rate of degradant formation on storage is reduced. As used herein, the term "degradant" refers to an undesired substance in a composition. In some embodiments, degradants may be formed via degradation of one or more components of the antiseptic solution. In some embodiments, degradants may be formed via degradation of the pH-dependent antimicrobial agent.

According to some aspects, the antiseptic solution may have a pH on storage such that the rate of degradant formation on storage is lower than the rate of degradant formation on storage of an identical solution except without having a pH-lowering agent, as described herein. For example, according to some aspects, the antiseptic solution may have a pH on storage such that the pH-dependent antimicrobial agent degrades at a slower rate than it would degrade in a solution with a higher pH. According to some aspects, the antiseptic solution may have a pH on storage such that the pH-dependent antimicrobial agent degrades at a slower rate than it would degrade in a solution with a pH within the operative pH range.

According to some aspects, the antiseptic solution may have a pH on storage such that the antiseptic solution is stable for a certain period of shelf life. According to some aspects, the antiseptic solution may have a pH on storage such that the antiseptic solution has a lower concentration of degradants after a certain period of shelf life than an identical solution except without having a pH-lowering agent, as described herein. In some embodiments, the antiseptic solution may have a pH on storage such that the antiseptic solution has a lower concentration of degradants after a certain period of shelf life than a similar antiseptic solution with a pH within the operative pH range.

According to some aspects, the period of shelf life of the antiseptic solution may be at least 1 month, preferably at least 2 months, more preferably at least 3 months, more preferably at least 4 months, more preferably at least 5 months, more preferably at least 6 months, more preferably at least 7 months, more preferably at least 8 months, more preferably at least 9 months, more preferably at least 10 months, more preferably at least 11 months, more at least 12 months, preferably at least 13 months, more preferably at least 14 months, more preferably at least 15 months, more preferably 1 at least 6 months, more preferably at least 17 months, more preferably at least 18 months, more preferably at least 19 months, more preferably at least 20 months, more preferably at least 21 months, more preferably at least 22 months, more preferably at least 23 months, more preferably at least 24 months, more preferably at least 25 months, more preferably at least 26 months, more preferably at least 27 months, more preferably at least 28 months, more preferably at least 29 months, more preferably at least 30 months, more preferably at least 31 months, more preferably at least 32 months, more preferably at least 33 months, more preferably at least 34 months, more preferably at least 35 months, and most preferably at least 36 months.

According to some aspects, the solution may comprise a pH-lowering agent. As used herein, the term "pH-lowering agent" refers to a component of the antiseptic solution selected to lower the solution's pH. In some embodiments, the pH-lowering agent may be present in the antiseptic solution such that the solution has a pH on storage as described herein. According to some aspects, the presence of the pH-lowering agent lowers the pH of the antiseptic solution from the operative pH range to the pH on storage. In other words, according to some aspects, an antiseptic solution without the pH-lowering agent may have a pH within the operative pH range, while the same antiseptic solution containing the pH-lowering agent may have a pH on storage as described herein.

According to some aspects, the pH-lowering agent may comprise a compound which reversibly reacts with one or more components of the antiseptic solution in order to lower the pH of the solution. An example of a pH-lowering agent which reversibly reacts with components of the antiseptic solution includes, but is not limited to, carbon dioxide.

According to some aspects, the pH-lowering agent may comprise a gas. For example, according to some aspects, the pH-lowering agent may comprise a gas which has been bubbled through the antiseptic solution prior to the antiseptic solution being contained within a sealed container (e.g., an ampoule of an applicator), such that the antiseptic solution comprises a concentration of the gas above the normal atmospheric concentration. For example, according to some aspects, the pH-lowering agent may comprise gaseous carbon dioxide. According to some aspects, the gaseous pH-lowering agent may be bubbled through the chilled antiseptic solution (e.g., chilled at approximately 2-8° C.). Gaseous carbon dioxide, for example, may then reversibly react with water in the antiseptic solution to reversibly form carbonic acid, thereby resulting in a decrease of the pH of the antiseptic solution.

According to some aspects, the pH-lowering agent may comprise an acid. As used herein, the term "acid" refers to a compound that acts as a proton (hydrogen ion) donor. According to some aspects, the pH-lowering agent may comprise one or more of, but not limited to, acetic acid, adipic acid, ascorbic acid, citric acid, hydrochloric acid, gluconic acid, lactic acid, malic acid, phosphoric acid, pyrophosphoric acid, succinic acid, sulfuric acid, tartaric acid, and/or trifluoroacetic acid.

According to some aspects, the solution may have second pH after storage, wherein the second pH is within the operative pH range. According to some aspects, the solution may have a second pH upon activation. As used herein, the term "activation" refers to a certain event immediately or shortly after storage which elicits a change in the antiseptic solution's pH.

In some embodiments, activation comprises contacting the antiseptic solution with a surrounding atmosphere, for example, by opening a sealed container in which the solution has been stored (e.g., an internal chamber or an ampoule within an internal chamber of an applicator) and/or releasing the solution from the container. According to some aspects, contacting the antiseptic solution with a surrounding atmosphere allows all or a portion of a gaseous pH-lowering agent to be released from the solution, such that the gaseous pH-lowering agent is no longer present or present at a reduced concentration in the solution, and thus no longer capable of reversibly reacting with components thereof. As a result, without the presence of the pH-lowering agent, the pH of the antiseptic solution will increase.

For example, in one embodiment, an antiseptic solution comprising gaseous carbon dioxide may have a pH on storage when contained within an ampoule of an applicator. In this example, the ampoule may become fractured, crushed, or otherwise opened, thereby releasing the antiseptic solution therefrom and allowing the solution to contact a surrounding atmosphere. Upon the solution's release from the ampoule, gaseous carbon dioxide may be released from the solution and into the surrounding atmosphere. In this example, as the concentration of carbon dioxide in the solution decreases, the carbonic acid in the solution will simultaneously convert into carbon dioxide and water, and the formed carbon dioxide will subsequently also be released from the solution. In this way, the pH of the solution will increase as the concentration of carbonic acid in the solution decreases.

According to some aspects, the solution will have a second pH immediately upon activation. According to some aspects, the solution will have a second pH shortly following activation. For example, in some embodiments, the solution will have a second pH within about 120 seconds after activation, preferably within about 90 seconds after activation, more preferably within about 60 second after activation, and most preferably within about 30 second after activation. According some aspects, the solution will have a second pH when it is applied to a surface.

In some embodiments, activation comprises contacting the antiseptic solution with an interaction agent. As used herein, the term "interaction agent" refers to a component that interacts with a pH-lowering agent in an antiseptic solution to increase the pH of the antiseptic solution.

According to some aspects, the interaction agent may comprise a neutralizing agent. As used herein, the term "neutralizing agent" refers to a component that chemically reacts with the pH-lowering agent in an antiseptic solution such that the pH-lowering agent is at least partially converted to a component that does not lower the pH of the antiseptic solution. According to some aspects, the neutralizing agent may react with an acidic pH-lowering agent. Example neutralizing agents include but are not limited to sodium bicarbonate, sodium carbonate, carbonate (e.g., using $CO_2$), and potassium carbonate. According to some aspects, the neutralizing agent may be the same as or comprise a scavenging agent, as described herein. According to some aspects, the reaction between the neutralizing agent and the pH-lowering agent may result in the formation of salt compounds which do not impact the microbiological efficacy of the pH-dependent antimicrobial agent.

According to some aspects, the neutralizing agent may react with all or a portion of the pH-lowering agent in the antiseptic solution. In some embodiments, the neutralizing agent may react with at least 50% of the pH-lowering agent in the antiseptic solution, preferably at least 60%, more preferably at least 70%, even more preferably at least 80%, even more preferably at least 90%, and most preferably 100%.

According to some aspects, the interaction agent may comprise a scavenging agent. As used herein, the term "scavenging agent" refers to a component that removes the pH-lowering agent from an antiseptic solution, resulting in an increase in the antiseptic solution's pH.

According to some aspects, the scavenging agent may comprise a functional group that interacts with (e.g., binds to), preferably selectively interacts with, the pH-lowering agent. For example, the scavenging agent may comprise an ion exchange resin, e.g., an anionic exchange resin. Examples of suitable scavenging agents include but are not limited to ion-exchange polymers. Examples of suitable ion-exchange polymers include but are not limited to Dowex® 66 free base anion exchange resin, AMBER-LITE™ IRA96 anion exchange resin, and Amberlyst® A21 free base anion exchange resin, and ScavengePore™ phenethyl diethylamine.

According to some aspects, the scavenging agent may remove all or a portion of the pH-lowering agent in the antiseptic solution. In some embodiments, the scavenging agent may remove at least 50% of the pH-lowering agent in the antiseptic solution, preferably at least 60%, more preferably at least 70%, even more preferably at least 80%, even more preferably at least 90%, and most preferably 100%.

In some preferred embodiments, activation may result in minimal or no impact to the chemical integrity of the pH-dependent antimicrobial agent. According to some aspects, activation may result in a chemical change in less than about 10% of the pH-dependent antimicrobial agent. According to some aspects, activation may result in minimal or no impact on the total related substances in the antiseptic solution, and/or results in little or no formation of any additional impurities in the antiseptic solution that were not present prior to activation. According to some aspects, activation may results in less than about a 10% increase of total related substances as compared to an identical solution that has not been activated. According to some aspects, activation may results in less than about a 10% increase of impurities as compared to an identical solution that has not been activated.

According to some aspects, the antiseptic solution may be provided in an applicator configured to apply the antiseptic solution to a surface. In some embodiments, the surface may be animal skin or human skin.

According to some aspects of the present invention, the applicator includes a body, an internal chamber for containing the antiseptic solution, and an application member. According to some aspects, the applicator may further comprise an ampoule received in the internal chamber, wherein the antiseptic solution is contained within the ampoule. According to some aspects, the applicator may also a pledget positioned between the application member and internal chamber, wherein the pledget may help control the rate liquid flows from the body and/or prevent shards of glass from pushing through application member during use of the applicator. According to some aspects, the pledget and/or application member may be provided with an interaction agent so that when antiseptic solution passes through the pledget and/or into the application member, one or more components of the antiseptic solution interacts with the interaction agent. That is, according to some embodiments, "activation" may refer to when the antiseptic solution passes through the pledget and/or into the application member provided with the interaction agent.

Some applicators which may be used in accordance with aspects of the present invention rely on various means of actuation to release a self-contained reservoir of an antiseptic solution for sterilization of the patient's skin. For example, a number of applicators are designed with a puncturing means. These applicators typically include a head with a spike, for example, and a sealed container or cartridge. A push or screw motion is employed to axially translate the head toward the sealed container so that the spike may pierce the sealed container and effectuate the release of the solution contained therein. Some examples of applicators using a puncturing means include U.S. Pat. Nos. 4,415,288; 4,498,796; 5,769,552; 6,488,665; and 7,201,525; and U.S. Pat. Pub. No. 2006/0039742, each incorporated by reference.

Other applicators which may be used in accordance with aspects of the present invention rely on breaking an internally situated frangible ampoule through the application of a one-way directional force or a localized application of pressure. The directional force is typically applied longitudinally to one end of the ampoule by a pushing motion designed to force the ampoule to break under a compressive stress, sometimes at a predetermined area of stress concentration. Alternatively, a pressure may be applied to a localized section of the ampoule through a squeezing motion designed to crush a section of the frangible ampoule in order to release the antimicrobial solution contained therein. Some examples of applicators using frangible ampoules in the manner discussed above include U.S. Pat. Nos. 3,757,782; 5,288,159; 5,308,180; 5,435,660; 5,445,462; 5,658,084; 5,772,346; 5,791,801; 5,927,884; 6,371,675; and 6,916,133, 7,182,536, each incorporated by reference.

Other applicators which may be used in accordance with aspects of the present invention include other methods of releasing antiseptic solution, such as in U.S. Pat. Nos. 8,708,983; 8,899,859; and 9,265,923; and U.S. Pat. Pub. No. 2013/0251439, each incorporated by reference.

Other related art applicators include those described in U.S. Pat. No. 9,119,946, U.S. Pat. Pub. No. 2011/0319842; U.S. application Ser. No. 14/595,084, entitled "Antiseptic Applicator," filed Jan. 12, 2015; and U.S. application Ser. No. 14/566,608, entitled "Antiseptic Applicator," filed Dec. 10, 2014, each incorporated by reference.

Various aspects of an antiseptic applicator may be illustrated with reference to one or more exemplary embodiments. As used herein, the term "exemplary" means "serving as an example, instance, or illustration," and should not necessarily be construed as preferred or advantageous over other embodiments of an antiseptic applicator disclosed herein.

FIG. 1 shows an example of an antiseptic applicator 10 which may be used in accordance with the present invention. Antiseptic applicator 10 generally includes a body 12, and an application member 16 secured to flange of body 12 and a lever 26. A frangible ampoule 14 for containing antiseptic solution is received in body 12. One end is closed with cap 19. Body 12 includes an internal chamber 22. The wall of the applicator includes thinner wall 40. The thickness of the wall of body 12 is reduced around crush area 42. Thin wall 40 makes it easier for crush portion 36 of lever 26 to fracture ampoule 14 when lever 26 is depressed. Pledget 46 is positioned between application member 16 and ampoule 14. Pledget 46 helps control the rate liquid flows from the body and/or prevents shards of glass from pushing through application member 16 during use of the applicator. Lever 26 includes hinge portion 38, crush portion 36 and handling portion 34 extending from the distal end of lever 26. When the lever 26 is depressed, force is transferred into the crush portion 36 of the lever 26.

According to some aspects, the pledget 46 may be impregnated or otherwise provided with the interaction agent. The foam application member 16 may comprise a single uniform piece of foam, which may additionally or alternatively be impregnated or otherwise provided with the interaction agent. In this example applicator of FIG. 1, the antiseptic solution is released by actuating the lever 26 with enough force for the ampoule 14 to break.

Figure 2:
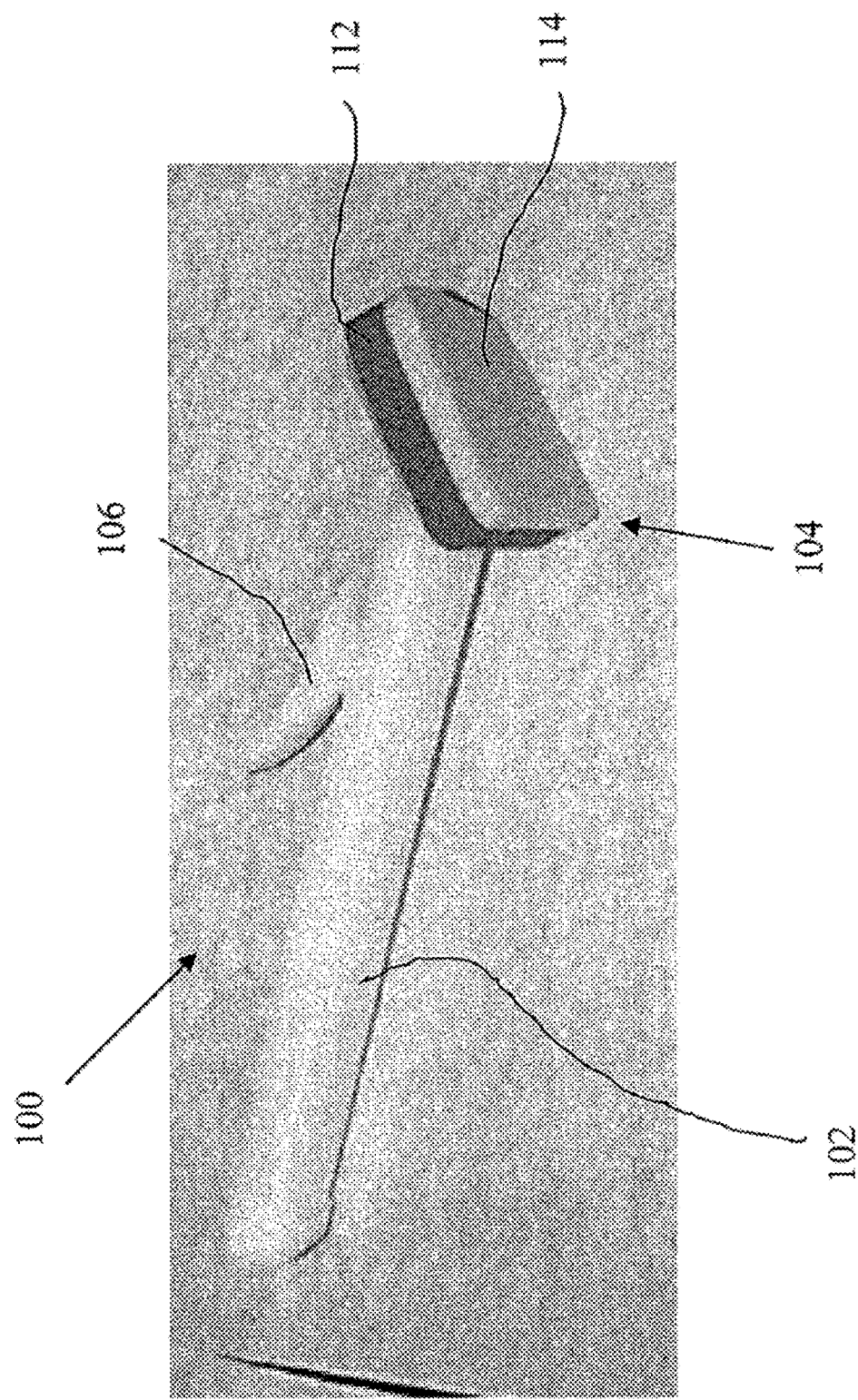
FIG. 2 is a perspective view of an antiseptic applicator in accordance with certain aspects of the present invention.
Figure 3:
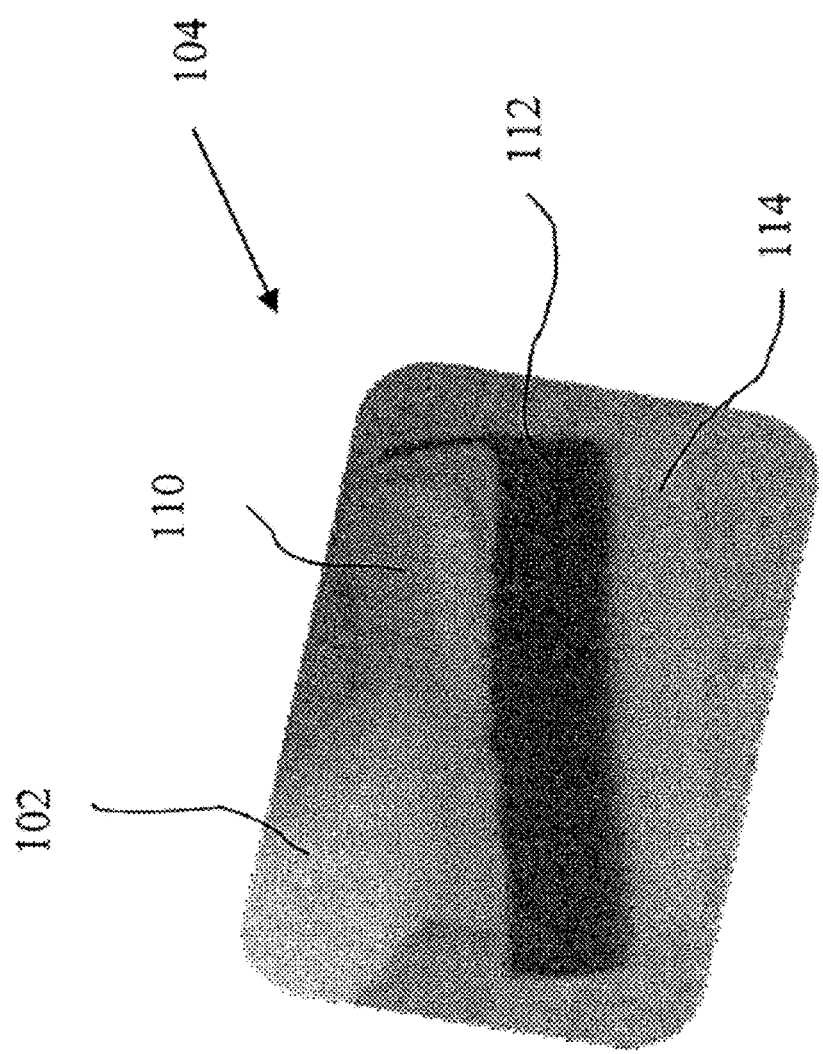
FIG. 3 is a perspective view of the head portion of the antiseptic applicator of FIG. 2.

FIGS. 2 and 3 show another example antiseptic applicator 100 that may be used in accordance with aspects of the present invention. As shown in FIGS. 2 and 3, the applicator 100 may comprise a substantially hollow container 102 containing or forming a fluid chamber, a head portion 110 coupled to a distal end of the container 102, and an application member 104 mounted to the head portion 110. The head portion 110 may include a proximal end, a distal end, and an interior portion defining a fluid chamber. As shown in FIG. 3, a proximal end of the head portion 110 may be attached to the distal end of the container 102, while the distal end of the head portion 110 may be attached to the application member 104. Thus, the head portion 110 may be disposed between the container 102 and the application member 104. The applicator 100 may include an actuating arm 106, that, when depressed releases antiseptic solution stored in the container 102. Various example mechanisms and methods for releasing antiseptic solution from the container into the chamber of the head portion are included in the above-listed related art references, each of which is incorporated by reference herein. It should be understood that all of the structure shown in FIG. 2 may be substituted with any suitable structure found in the cited related art applicators. That is, one having ordinary skill in the art may apply the application member 104 to any known antiseptic applicator by replacing the application member of the related art antiseptic applicator with the application member 104. For example, the application member 104 may be applied to any of the application members of the above-cited references. A pledget similar to the pledget shown in FIG. 1 may also be included in the antiseptic applicator 100.

The application member 104 may comprise a foam sponge material, for example, or any suitable material that allows the controlled application of the contained solution from the container 102 to a surface external to the applicator 100. For example, the foam may comprise polyurethane foam. The foam may be hydrophilic or hydrophobic, depending on the antiseptic solution contained in the container. Suitable foams or other materials for the application member 104 may be found in the related applicators. In accordance with aspects of the present invention, the application member 104 may be impregnated with the interaction agent. In some embodiments, the application member 104 may include a first layer 112 and a second layer 114, wherein either the first layer 112 or the second layer 114 may be impregnated or otherwise provided with the interaction agent. The first layer and/or second layer may be impregnated with the interaction agent by spray coating, dipping the foam into the interaction agent and allowing it to be adsorbed thereon, or mixing the interaction agent into the foam base as the foam is formed, for example. As shown in FIG. 3, the first foam layer 112 may be positioned or disposed toward the distal end of the head portion 110, and the second foam layer 114 may be disposed away from the distal end of the head portion 110. In other words, the first foam layer may be the portion of the application member that is attached to the head portion, while the second foam layer may be the portion that contacts the patient's skin during use. Thus, in this arrangement, during application, the antiseptic solution first passes through the first foam layer and then passes through the second foam layer. The foam material chosen may be porous with a particular soak rate, for example, or may be provided with structural features, including slits or apertures, to direct and control the flow rate of the solution through the application member 104. The first and second foam layers may comprise the same or different foam materials. Additionally, the first and second foam layers may be integral with each other. In other words, the application member 104 may be formed from a single piece of foam. When the first and second foam layers are formed from separate pieces, the layers may be connected by a porous adhesive, sonic lamination, or heat lamination, for example.

The container 102 is preferably a self-contained structure, formed of a suitable material, such as a plastic, e.g., a high-density polyethylene plastic, that is flexible, yet resistant to deformation and chemical leaching. The container 102 may be generally hollow so as to directly contain antiseptic solution or to contain an ampoule, pouch, or the like that stores antiseptic solution. Any of the antiseptic solution releasing mechanisms of the related art applicators that allow the solution to flow from the container 102 into the chamber of the head portion may be implemented in the applicator of the instant invention. This may include devices that puncture an ampoule, tear a pouch, lift a plug, or otherwise provide a fluid pathway for antiseptic solution to flow into the chamber of the head portion. In the variation shown in FIG. 2, the antiseptic solution releasing mechanism includes actuating arm 106, which may be squeezed toward the fluid container 102 to puncture or break an ampoule having antiseptic solution contained therein.

The present invention also provides for methods of using the antiseptic solutions and/or applicators as described herein. According to some aspects, the antiseptic solutions and/or applicators of the present invention may be used for disinfecting a surface. Preferably, the antiseptic solutions and/or applicators of the present invention may be used for disinfecting a surface prior to a medical procedure, for example, by applying the antiseptic solution to a patient's skin to kill microorganisms prior to performing the medical procedure. The patient may be an animal or a human.

The present invention is further described by way of the following non-limiting examples that are given for illustrative purposes only.

EXAMPLES

Example 1: Effect of pH on pH-Dependent Antimicrobial Agent Degradation

In this example, the impact of an antiseptic solution's pH on the degradation rate of a pH-dependent antimicrobial agent, chlorhexidine gluconate, was investigated.

A bulk antiseptic solution containing 2% w/v chlorhexidine gluconate in 70% v/v isopropyl alcohol and having an apparent pH of 7.6 was first divided into four separate fractions. Each of the first three fractions was adjusted to an apparent pH of around 4.5 using acetic acid, citric acid, and hydrochloric acid, respectively. One fraction was used as a control.

The four fractions were then sealed within four separate glass ampoules. Next, each of the glass ampoules was heated at about 110° C. for about 30 minutes using an oil bath, and then cooled. After cooling to room temperature, each of the fractions was measured for total related substances (TRS) using a validated analytical test method. The formation of total related substances indicates degradation of the pH-dependent antimicrobial agent.

Table 1 shows the change in total related substances (ΔTRS) for each of the fractions after heating, along with the percentage of degradation relative to the control.

TABLE 1

| Solution | Apparent pH | ΔTRS | % Degradation Relative to Control |
|---|---|---|---|
| Acetic Acid | 4.49 | 0.59% | 29% |
| Citric Acid | 4.45 | 0.27% | 13% |

TABLE 1-continued

| Solution | Apparent pH | ΔTRS | % Degradation Relative to Control |
|---|---|---|---|
| HCl | 4.60 | ~0.4% | 21% |
| Control | 7.58 | 2.05% | N/A |

As shown in Table 1, the fractions whose pH were lowered with acetic acid, citric acid, or hydrochloric acid showed a substantially lower change in total related substances compared to the control fraction, indicating that these fractions provide a lower pH-dependent antimicrobial degradation rate than the control fraction.

Example 2: Effect of pH on pH-Dependent Antimicrobial Agent Degradation

In this example, the impact of an antiseptic solution's pH on the degradation rate of about 2% w/v chlorhexidine gluconate in 70% v/v isopropyl alcohol (having an initial apparent pH of 7.6) was investigated.

A bulk antiseptic solution was first divided into ten separate fractions. The pH of nine of the fractions was adjusted using a pH-lowering agent (either gluconic acid, acetic acid, or citric acid), as shown in Table 2. One fraction was used as a control.

TABLE 2

| Fraction | pH lowering agent | pH |
|---|---|---|
| 1 | Gluconic Acid | 4.8 |
| 2 | Gluconic Acid | 5.5 |
| 3 | Gluconic Acid | 6.5 |
| 4 | Acetic Acid | 4.5 |
| 5 | Acetic Acid | 5.3 |
| 6 | Acetic Acid | 5.8 |
| 7 | Citric Acid | 4.5 |
| 8 | Citric Acid | 5.3 |
| 9 | Citric Acid | 5.8 |
| 10 | Control | 7.3 |

Figure 5:
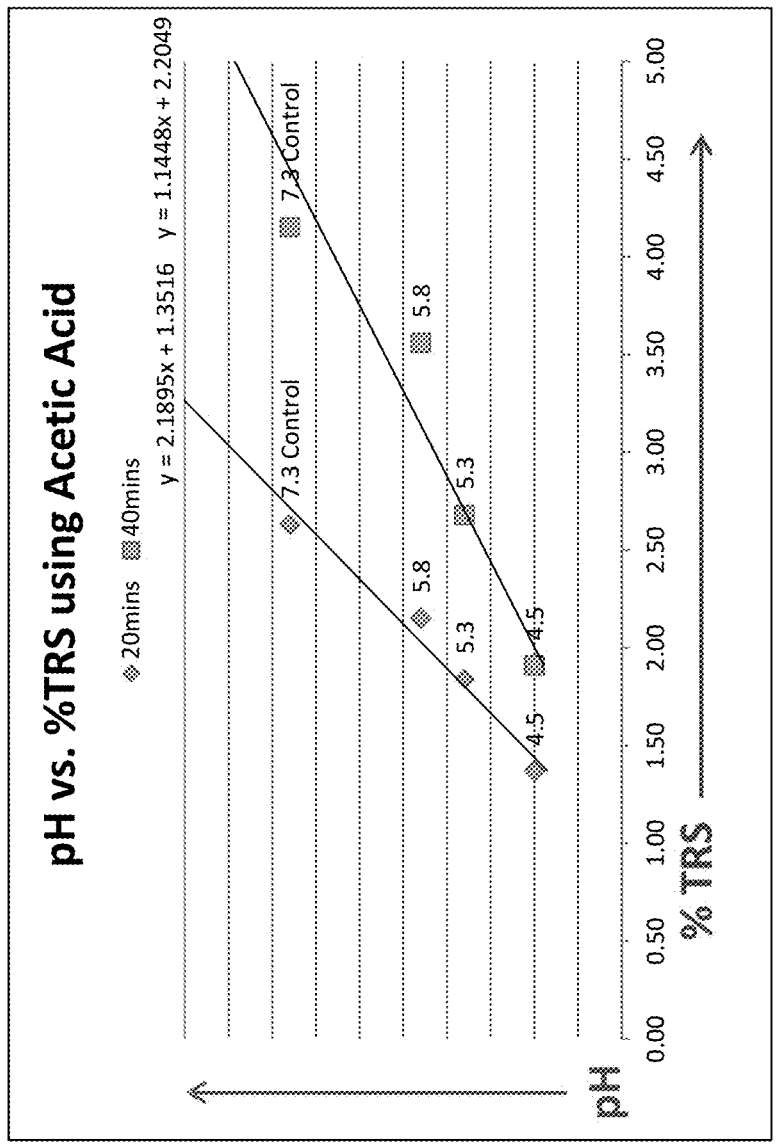
FIG. 5 shows pH vs. concentration of total related substances in solutions comprising acetic acid as a pH-lowering agent, as described in Example 2.
Figure 6:
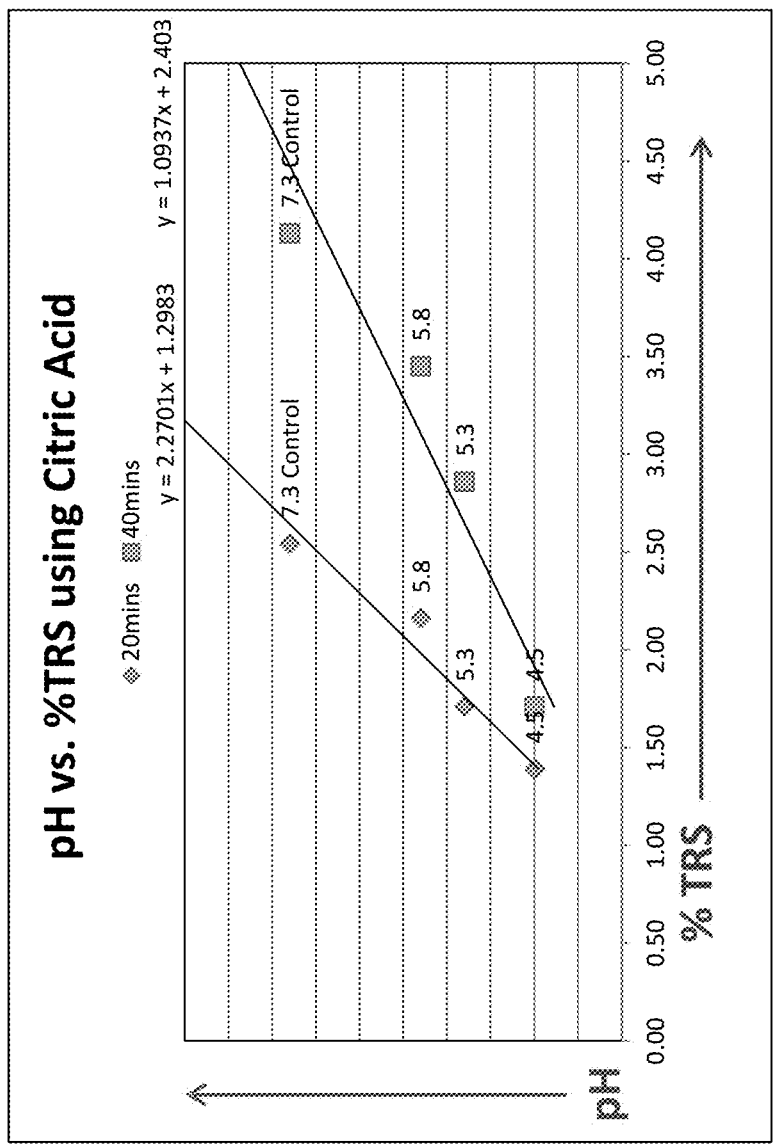
FIG. 6 shows pH vs. concentration of total related substances in solutions comprising citric acid as a pH-lowering agent, as described in Example 2.

The ten fractions were then sealed within separate glass ampoules. Next, each of the glass ampoules was heated at about 115° C. for about 20 minutes, and the fractions were then tested for total related substances. Each of the glass ampoules was then heated at about 115° C. for an additional 20 minutes (40 minutes total), and then again tested for total related substances. The results of this test are shown in FIGS. 4-6.

Figure 4:
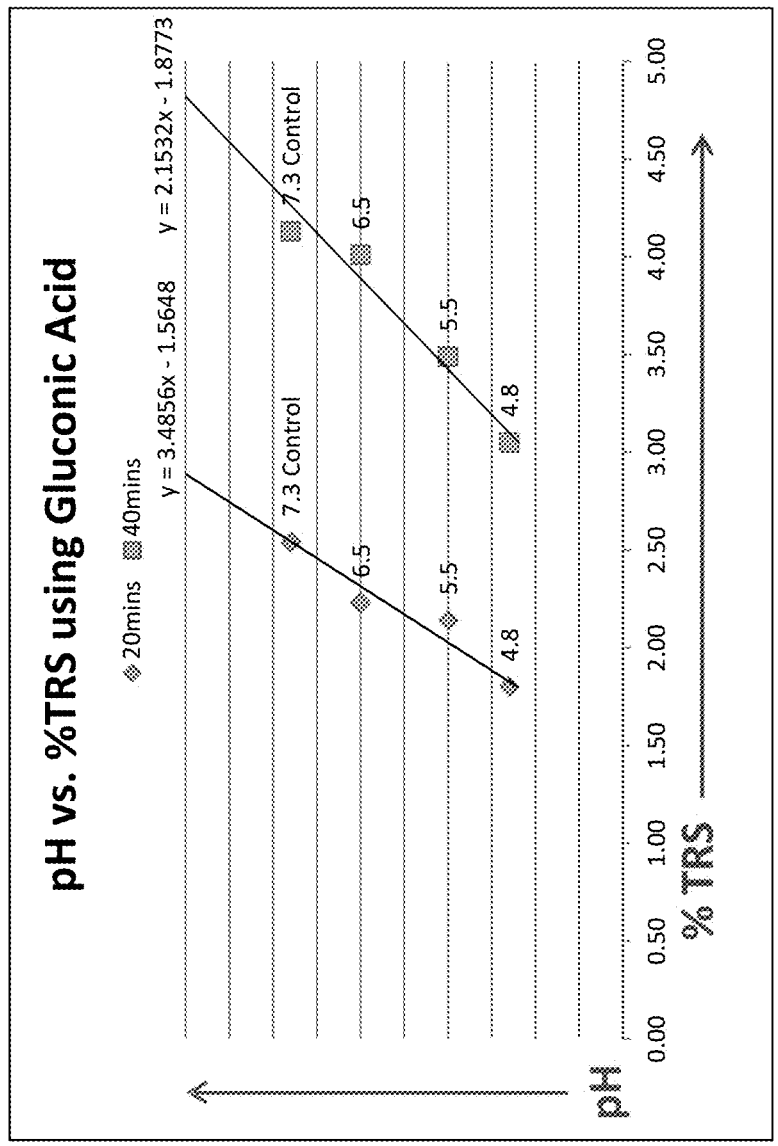
FIG. 4 shows pH vs. concentration of total related substances in solutions comprising gluconic acid as a pH-lowering agent, as described in Example 2.

For example, FIG. 4 shows the correlation between pH and concentration of total related substances after 20 minutes and 40 minutes of heating at about 115° C. As noted in Example 1, the formation of total related substances indicates degradation of the pH-dependent antimicrobial agent. As shown in FIG. 4, a substantially lower concentration of total related substances (and thus, degradation rate) was observed for the fractions having pH values at or below about 5.5, both after 20 minutes and 40 minutes of heating. FIGS. 5 and 6 show similar trends for fractions whose pH was adjusted using acetic acid and citric acid, respectively. Moreover, none of solutions 1-9 showed related substances that were not also present in the control solution.

Example 3: Neutralizing a pH-Lowering Agent in an Antiseptic Solution

In this example, four antiseptic solutions were prepared. Each solution contained about 2% w/v chlorhexidine gluconate in 70% v/v isopropyl alcohol. The pH of each solution was adjusted to a pH of about 4.5 using a pH-lowering agent.

The samples were then subjected to a foam pledget either with or without a neutralizing agent (sodium bicarbonate) embedded therein. Specifically, Solution 1 was passed through a pledget without the neutralizing agent, Solution 2 was not subjected to a pledget, Solution 3 was passed through a pledget embedded with the neutralizing agent, and Solution 4 was aggressively stirred/soaked in a pledget embedded with the neutralizing agent.

After the treatment with the foam pledgets, the pH of the solutions was measured, as shown in Table 3 below:

TABLE 3

| Solution | pH |
|---|---|
| 1 | 4.5 |
| 2 | 4.5 |
| 3 | 6.0 |
| 4 | 6.0 |

As shown in Table 3, the solutions subjected to a foam pledget embedded with the neutralizing agent (Solution 3 and 4) showed a substantially higher pH than the solutions which were subjected to a foam pledget without the neutralizing agent (Solution 1) and not subjected to a foam pledget (Solution 2).

After the treatment, the concentration of chlorhexidine gluconate and total related substances was also measured for each solution. As shown in Table 4, neutralization using the neutralizing agent did not substantially impact the chlorhexidine gluconate (CHG) concentration or total related substances (TRS) concentration. Moreover, the use of the neutralizing agent did not result in the formation of any additional impurities that were not present in the solutions that were not subjected to the neutralizing agent.

TABLE 4

| Solution | CHG (% w/v) | TRS (% w/v) |
|---|---|---|
| 1 | 1.95 | 1.14 |
| 2 | 1.96 | 1.25 |
| 3 | 1.98 | 1.26 |
| 4 | 1.88 | 1.27 |

Example 4: Scavenging a pH-Lowering Agent in an Antiseptic Solution

In this example, a bulk antiseptic solution containing 2% w/v chlorhexidine gluconate in 70% v/v isopropyl alcohol was adjusted to an apparent pH of around 4.5 using a pH-lowering agent. Then, the solution was divided into separate fractions.

Three of the fractions were passed over a scavenging agent comprising an ion-exchange polymer (specifically, Dowex® 66 free base anion exchange resin). One fraction was not subjected to the scavenging agent and was used as a control.

The first three fractions were pooled, and the pH of the solution containing the pooled fractions was determined to be 5.7. Further analysis of the chemical characteristics of the antiseptic solutions using a validated test method was then performed, specifically to measure the concentration of chlorhexidine gluconate (CHG) in the pooled solution and the control solution. The results of this analysis are shown in FIG. 7 and Table 5.

Figure 7:
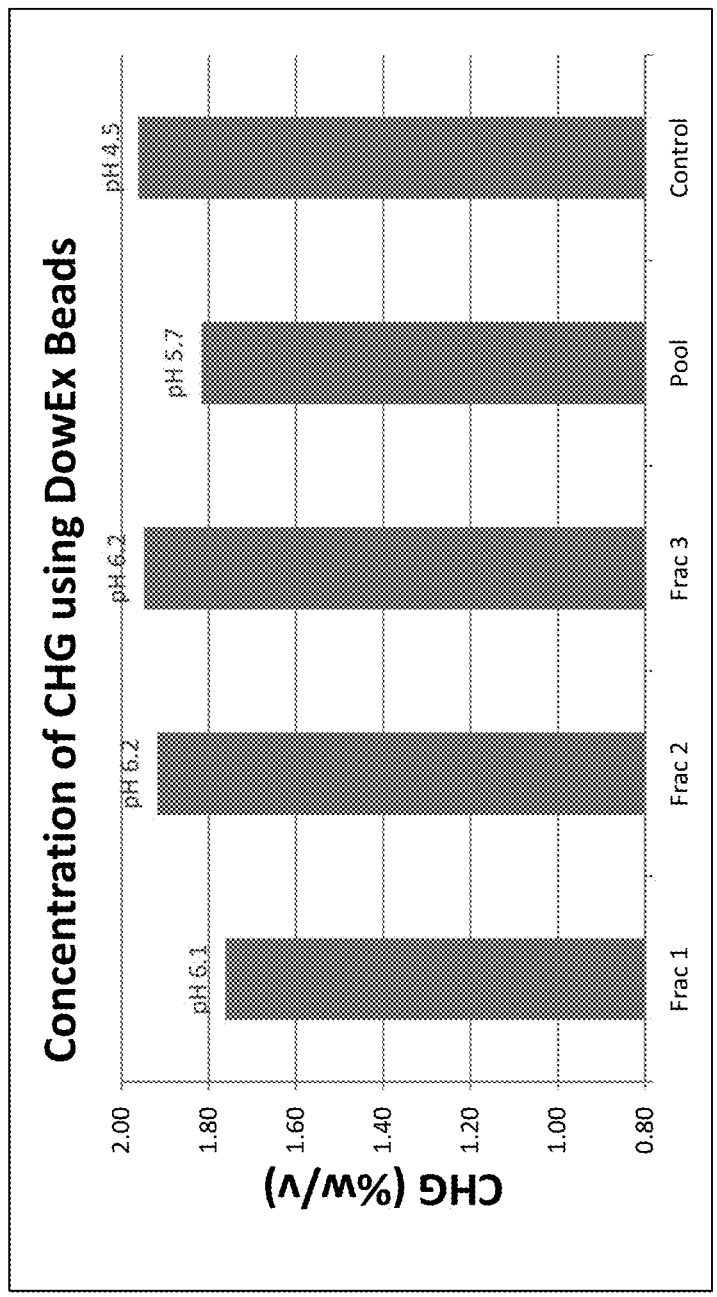
FIG. 7 shows the concentration of chlorhexidine gluconate in different antiseptic solution fractions using Dowex® 66 free base anion exchange resin as a scavenging agent, as described in Example 4.

In particular, FIG. 7 shows that scavenging the pH-lowering agent using DowEx beads resulted in minimal impact to the chlorhexidine gluconate content (<8%). Table 5 shows that scavenging the pH-lowering agent using DowEx beads did not substantially impact the concentration of total related substances (TRS).

TABLE 5

| Solution | TRS (% w/v) |
|---|---|
| Pooled | 1.82 |
| Control | 1.96 |

Moreover, scavenging the pH-lowering agent using DowEx beads did not result in the formation of any additional impurities that were not present in the control solution.

The same experiment was also performed using a different ion-exchange polymer (specifically, AMBERLITE™ IRA96 anion exchange resin) as a scavenging agent.

In this experiment, the pH of the solution containing the pooled fractions was determined to be 6.2. Further analysis of the chemical characteristics of the antiseptic solutions using a validated test method was then performed, specifically to measure the concentration of chlorhexidine gluconate (CHG) in the pooled solution and the control solution. The results of this analysis are shown in FIG. 8 and Table 6.

Figure 8:
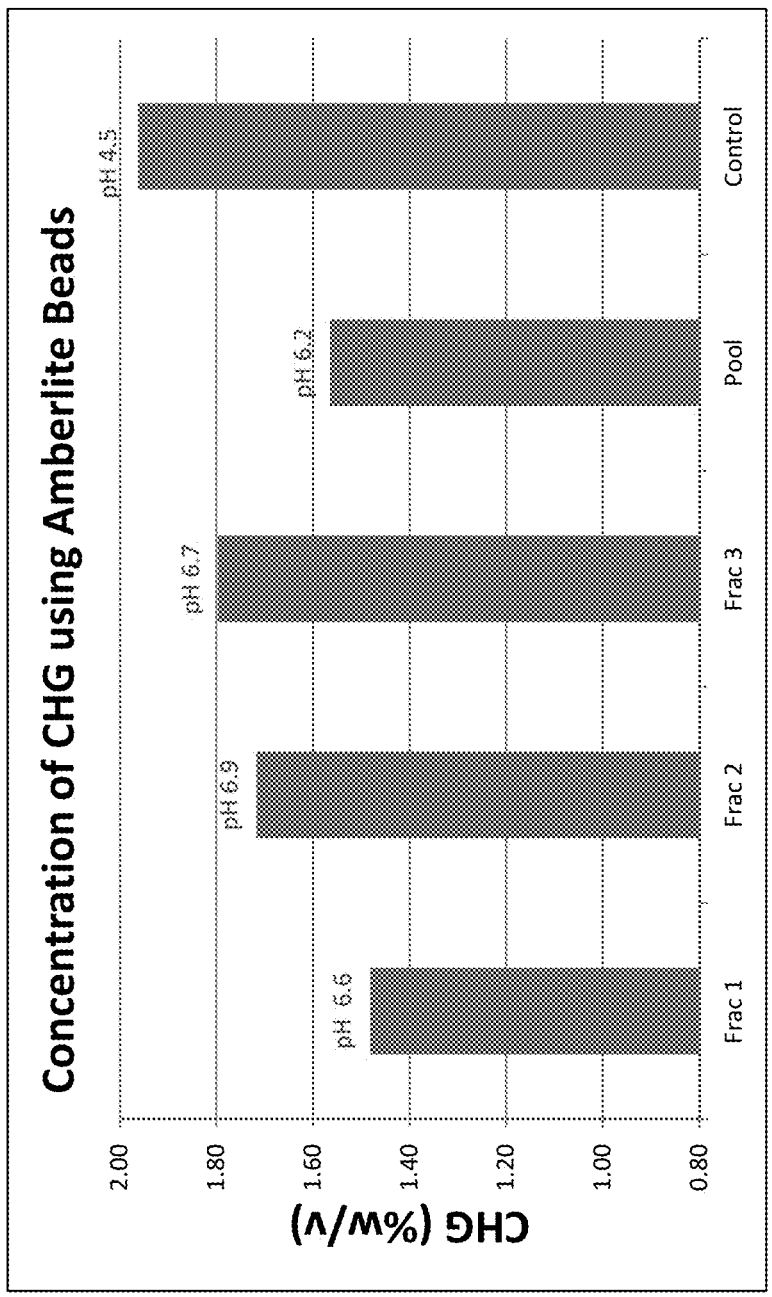
FIG. 8 shows the concentration of chlorhexidine gluconate in different antiseptic solution fractions using AMBERLITE™ IRA96 anion exchange resin as a scavenging agent, as described in Example 4.

In particular, FIG. 8 shows that scavenging the pH-lowering agent using Amberlite beads resulted in minimal impact to the chlorhexidine gluconate content. Table 6 shows that scavenging the pH-lowering agent using Amberlite beads also resulted in minimal impact to the concentration of total related substances (TRS).

TABLE 6

| Solution | TRS (% w/v) |
|---|---|
| Pooled | 1.56 |
| Control | 1.96 |

Moreover, scavenging the pH-lowering agent using Amberlite beads did not result in the formation of any additional impurities that were not present in the control solution.

The same experiment was then repeated using a different ion-exchange polymer (specifically, Amberlyst® A21 free base anion exchange resin) as a scavenging agent.

In this experiment, the pH of the solution containing the pooled fractions was determined to be 9.3. Further analysis of the chemical characteristics of the antiseptic solutions using a validated test method was then performed, specifically to measure the concentration of chlorhexidine gluconate (CHG) in the pooled solution and the control solution. The results of this analysis are shown in FIG. 9 and Table 7.

Figure 9:
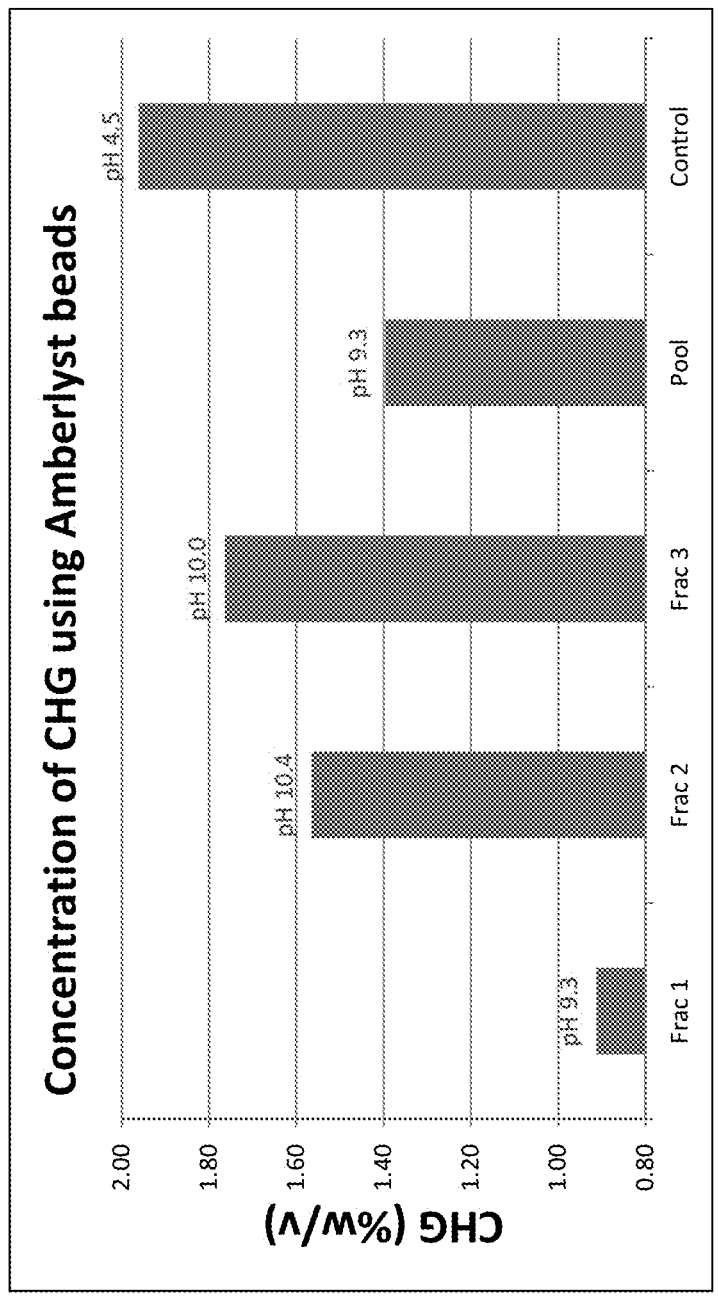
FIG. 9 shows the concentration of chlorhexidine gluconate in different antiseptic solution fractions using Amberlyst® A21 free base anion exchange resin as a scavenging agent, as described in Example 4.

In particular, FIG. 9 shows that scavenging the pH-lowering agent using Amberlyst beads resulted in minimal impact to the chlorhexidine gluconate content. Table 7 shows that scavenging the pH-lowering agent using Amberlyst beads also resulted in no impact to the concentration of total related substances (TRS).

TABLE 5

| Solution | TRS (% w/v) |
|---|---|
| Pooled | 1.96 |
| Control | 1.96 |

Moreover, scavenging the pH-lowering agent using Amberlyst beads did not result in the formation of any additional impurities that were not present in the control solution.

Example 5: Antimicrobial Effect of Antiseptic Solutions

In this example, the impact of an antiseptic solution's pH on microbiological efficacy of a pH-dependent antimicrobial agent, chlorhexidine gluconate, was investigated.

A bulk antiseptic solution containing 2% w/v chlorhexidine gluconate in 70% v/v isopropyl alcohol was first divided into six separate fractions. These six fractions were individually modified as follows:

| Fraction | Modification | Final Test pH |
|---|---|---|
| 1 | pH-lowering agent (gaseous carbon dioxide) added, then released | Operative range |
| 2 | Acidified with pH-lowering agent (trifluoroacetic acid) and subjected to neutralization with neutralizing agent (sodium bicarbonate) | Operative range |
| 3 | Acidified with pH-lowering agent (trifluoroacetic acid) and subjected to scavenging agent (DowEx resin) | Operative range |
| 4 | Acidified with pH-lowering agent (trifluoroacetic acid) and subjected to scavenging agent (Amberlyst resin) | Operative range |
| 5 | Acidified with pH-lowering agent (trifluoroacetic acid) to a pH of about 4.5 | 4.5 |
| 6 | None (Control Fraction) | Operative range |

All six fractions were then tested against *Staphylococcus aureus* ATCC 29213 at 100%, 10%, and 0.01% of the use concentration for chlorhexidine gluconate (i.e., three different test concentration samples for each of the six fractions, totaling 18 samples). The average log reduction of the bacteria was recorded after 30 seconds for the 100% and 10% samples, and after 15 minutes for the 0.01% samples. The results of the study are shown in FIG. 10.

Figure 10:
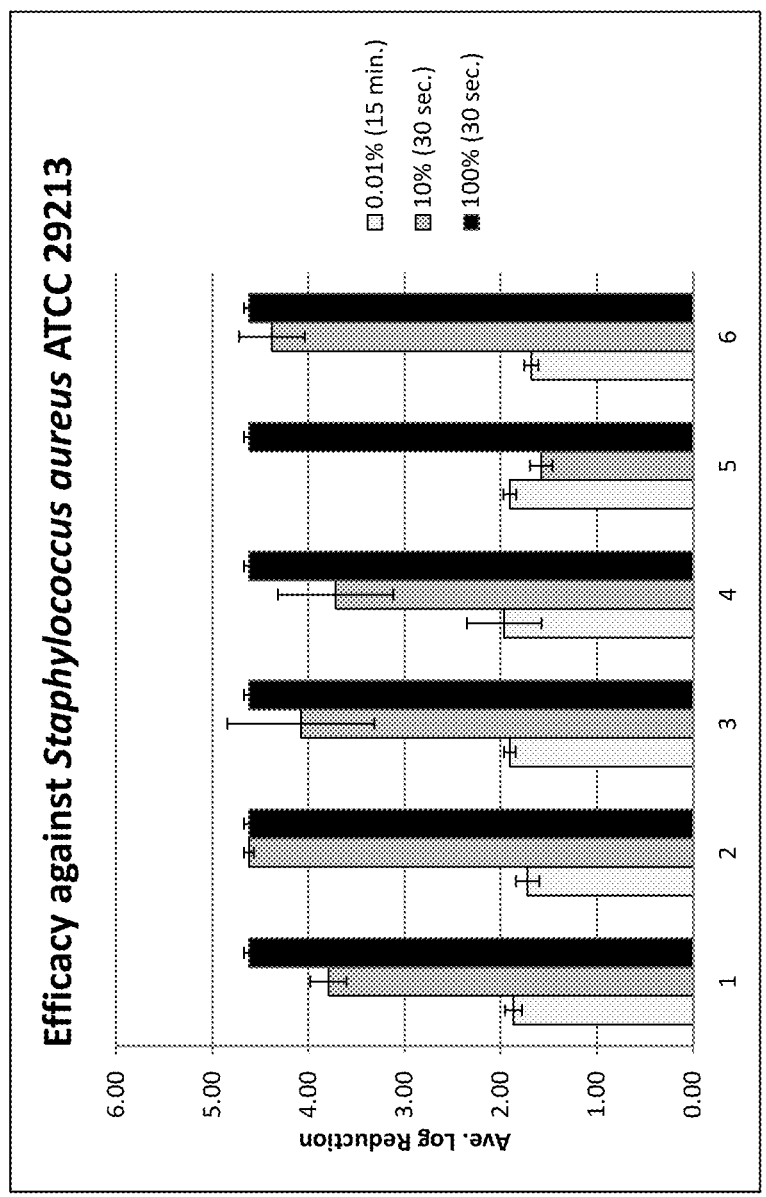
FIG. 10 shows the efficacy against *Staphylococcus aureus* ATCC 29213 in different antiseptic solution fractions, as described in Example 5.

In particular, FIG. 10 shows that, as expected, total kill of the bacteria was observed for all formulations at the 100% test concentration. However, at the 10% test concentration, Fraction 5 (i.e., the fraction whose pH was 4.5, or below the operative pH range) showed a lower average log reduction compared to the other fractions (i.e., the fractions whose pH were within the operative range). In general, no substantial difference was observed in the average log reduction for the other five formulations.

The results of this study indicate that a pH-dependent antimicrobial agent provided in a solution with a pH that is below the operative pH range (e.g., a pH of about 4.5) shows less than acceptable microbiological activity, as evidenced by the lower log reduction of Fraction 5 compared to the other five fractions. Moreover, no change in the microbiological efficacy was observed for antiseptic solutions subjected to carbon dioxide, acidified and subsequently neutralized, or acidified and subjected to scavenging compounds.

What is claimed is:

1. An antiseptic solution comprising:
   (A) a solvent;
   (B) a pH-lowering agent; and
   (C) a pH-dependent antimicrobial agent, the pH-dependent antimicrobial agent having an operative pH range,
   wherein the solution has a first pH on storage and a second pH upon activation;
   wherein the first pH is lower than the operative pH range, and the second pH is within the operative pH range; and
   wherein the solution is provided in an applicator configured to apply the solution to a surface, the applicator having (a) and (b) wherein (a) and (b) are:
   (a) a pledget, and
   (b) an application member
      wherein the pledget and/or the application member contains an interaction agent that interacts with the pH-lowering agent when the solution passes through the pledget and/or the application member, and wherein the pledget is disposed interior to the application member; and
   wherein the interaction agent in (a) and (b) comprises at least one of (i) and (ii):
      (i) a neutralizing agent that chemically reacts with the pH-lowering agent such that the pH-lowering agent is at least partially converted to a component that does not lower the pH of the solution, and
      (ii) a scavenging agent that removes at least a portion of the pH-lowering agent from the solution.

2. The antiseptic of claim 1, wherein the pH on storage is at least about 0.5 units lower than the operative pH range.

3. The antiseptic of claim 1, wherein the pH-dependent antimicrobial agent comprises chlorhexidine and/or a salt thereof.

4. The antiseptic of claim 1, wherein the operative pH range is about 5.5 and above.

5. The antiseptic of claim 1, wherein the first pH is lower than about 5.

6. The antiseptic of claim 1, wherein the pH-lowering agent reversibly reacts with at least one component in the solution to form an acid.

7. The antiseptic of claim 1, wherein the pH-lowering agent is gaseous carbon dioxide.

8. The antiseptic of claim 1, wherein the pH-lowering agent comprises an acid.

9. The antiseptic of claim of claim 1, wherein the scavenging agent comprises an ion exchange resin.

10. The antiseptic of claim of claim 1, wherein the neutralizing agent comprises sodium bicarbonate, sodium carbonate, carbonate, potassium carbonate, or a combination thereof.

* * * * *